US00PP35616P2

(12) United States Plant Patent
Gielis

(10) Patent No.: US PP35,616 P2
(45) Date of Patent: Jan. 30, 2024

(54) ***SEMPERVIVUM* PLANT NAMED 'BELSEMMAG2'**

(50) Latin Name: ***Sempervivum marmoreum* X *Sempervivum tectorum***
Varietal Denomination: Belsemmag2

(71) Applicant: Belgicactus B.V.B.A., Westerlo (BE)

(72) Inventor: Jef Gielis, Westerlo (BE)

(73) Assignee: BELGICACTUS B.V.B.A., Westerlo (BE)

( * ) Notice: Subject to any disclaimer, the term of this patent is extended or adjusted under 35 U.S.C. 154(b) by 0 days.

(21) Appl. No.: 18/139,811

(22) Filed: Apr. 26, 2023

(30) Foreign Application Priority Data

Nov. 30, 2022 (QZ) ..... PBR 2022/2726

(51) Int. Cl.
*A01H 5/12* (2018.01)
*A01H 6/32* (2018.01)

(52) U.S. Cl.
USPC ..... Plt./263.1
CPC ..... *A01H 6/32* (2018.05)

(58) Field of Classification Search
USPC ..... Plt./263.1
CPC ..... A01H 6/32; A01H 5/12
See application file for complete search history.

*Primary Examiner* — Keith O. Robinson
(74) *Attorney, Agent, or Firm* — Penny J. Aguirre

(57) ABSTRACT

A new cultivar of *Sempervivum* plant named 'Belsemmag2' characterized by its foliage that is dark burgundy red to nearly black with bright red new leaves in spring, turning to soft rose-red with green accents in summer, and red-purple and grey-green in autumn and winter, its strong root system, and its suitability for growing outdoors year around.

3 Drawing Sheets

Botanical classification: *Sempervivum marmoreum* X *Sempervivum tectorum.*
Variety Denomination: 'Belsemmag2'.

CROSS REFERENCE TO A RELATED APPLICATION

This application claims priority to European Community Plant Variety Office (CPVO) Application No. 2022/2726 filed on Nov. 30, 2022, under 35 U.S.C. 119(f), the entire contents of which is incorporated by reference herein. The information for the plant breeders' rights application was received directly from the Inventor.

BACKGROUND OF THE INVENTION

The present invention relates to a new and distinct cultivar of *Sempervivum* of hybrid origin and will be referred to hereinafter by its cultivar name, 'Belsemmag2'. The new cultivar of *Sempervivum* is a hardy succulent perennial grown for use as a landscape and container plant.

The new cultivar resulted from a controlled breeding program conducted by the Inventor in Westerlo, Belgium. The Inventor made a cross in 2011 between an unnamed and unpatented plant of *Sempervivum marmoreum* as the female parent and an unnamed and unpatented plant of *Sempervivum tectorum* in the Inventor's breeding program as the male parent. 'Belsemmag2' was selected as a single unique plant in 2013 from the resulting seedlings of the above cross.

Asexual propagation of the new cultivar was first accomplished by the Inventor by cuttings in 2013 in Westerlo, Belgium. Asexual propagation by cuttings and offshoots has determined the characteristics to be stable and reproduced true to type in successive generations.

SUMMARY OF THE INVENTION

The following traits have been repeatedly observed and are determined to be the characteristics of the new cultivar.

These attributes in combination distinguish 'Belsemmag2' as a unique cultivar of *Sempervivum.*

1. 'Belsemmag2' exhibits foliage that is dark burgundy red to nearly black with bright red new leaves in spring, turning to soft rose-red with green accents in summer, and red-purple and grey-green in autumn and winter.
2. 'Belsemmag2' exhibits a compact, well-branched rosette-shaped growth habit with many rosettes.
3. 'Belsemmag2' exhibits a strong root system.
4. 'Belsemmag2' exhibits suitability for growing outdoors year around.

The female parent of 'Belsemmag2' differs from 'Belsemmag2' in having foliage that is dull red-brown in color in spring and green in summer. The male parent of 'Belsemmag2' differs from 'Belsemmag2' in having foliage that is lighter in color; very pale red in color with light yellowish green accents. 'Belsemmag2' can be most closely compared to the *Sempervivum* cultivars 'Belsemred1' (U.S. Plant Pat. No. 31,919) and 'Bedivere' (not patented). 'Belsemred1' is similar to 'Belsemmag2' in growth habit and rosette size. 'Belsemred1' differs from 'Belsemmag2' in having foliage that changes less with the seasons; red to red-purple in spring to autumn and turning brown-purple in winter and lacks green coloration and more numerous and longer foliage hairs. 'Bedivere' is similar to 'Belsemmag2' in rosette size. 'Bedivere' differs from 'Belsemmag2' in having foliage that is pale orange-red with faded light green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Concept Plants, Planttipp and floraxchange.

BRIEF DESCRIPTION OF THE DRAWINGS

The accompanying color photographs illustrate the overall appearance and distinct characteristics of 1.8-year old plants of the new *Sempervivum* as grown outdoors in 13-cm containers in Westerlo, Belgium.

The photograph in FIG. 1 provides a top view of a plant of 'Belsemmag2' in spring.

Figure 1:
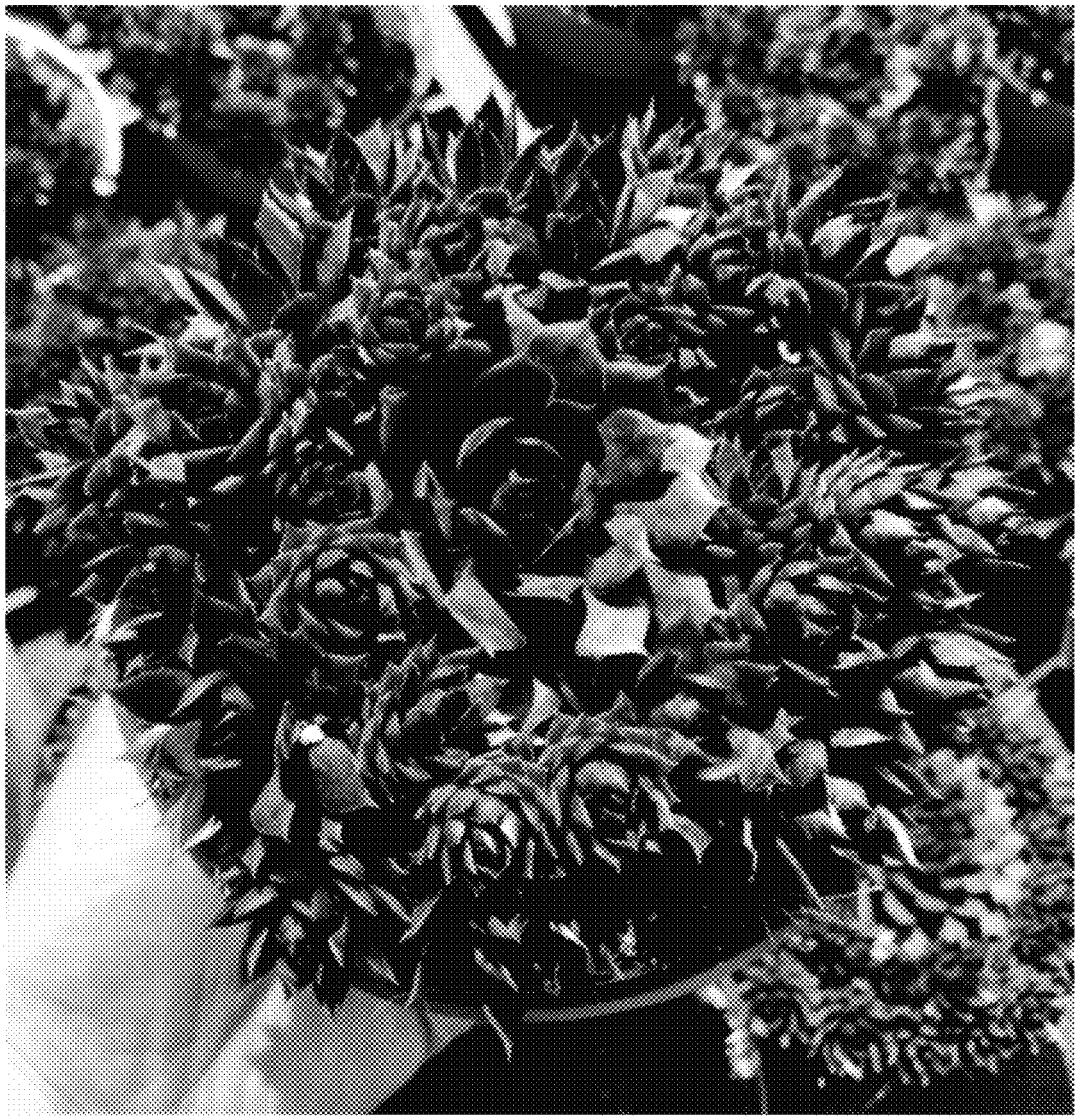
Figure 2:
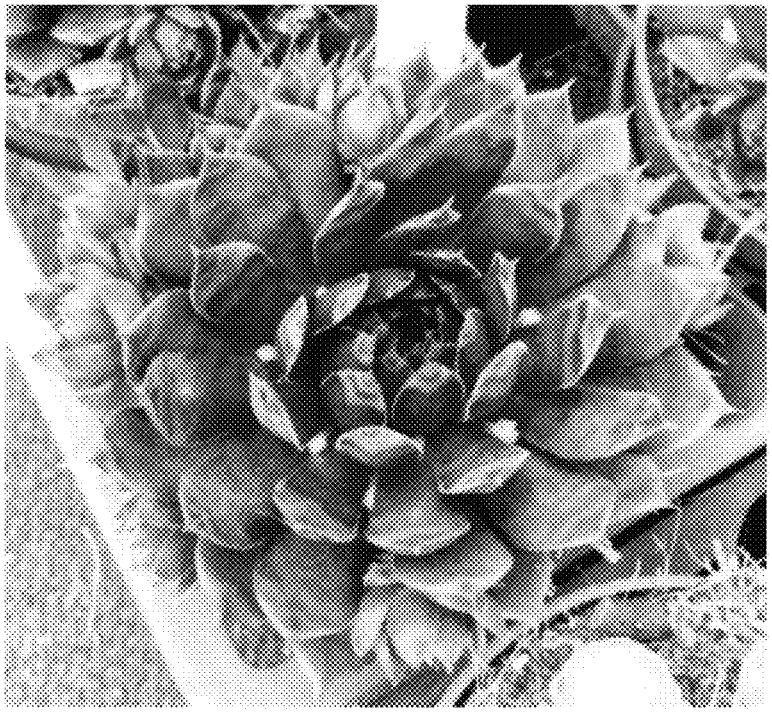

The photograph in FIG. 2 provides a top view of a plant of 'Belsemmag2' in summer.

Figure 3:
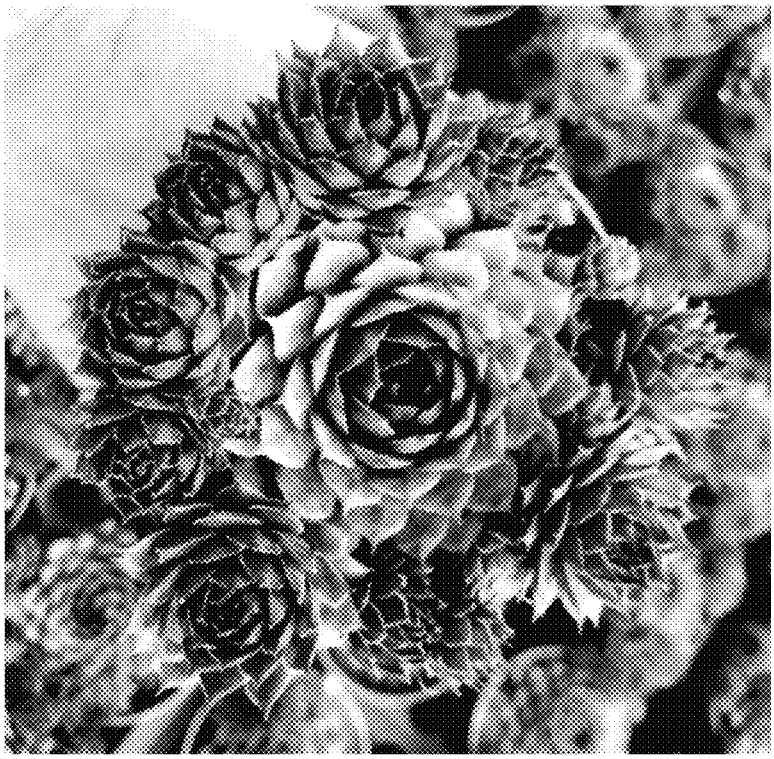

The photograph in FIG. 3 provides a top view of a plant of 'Belsemmag2' in autumn.

Figure 4:
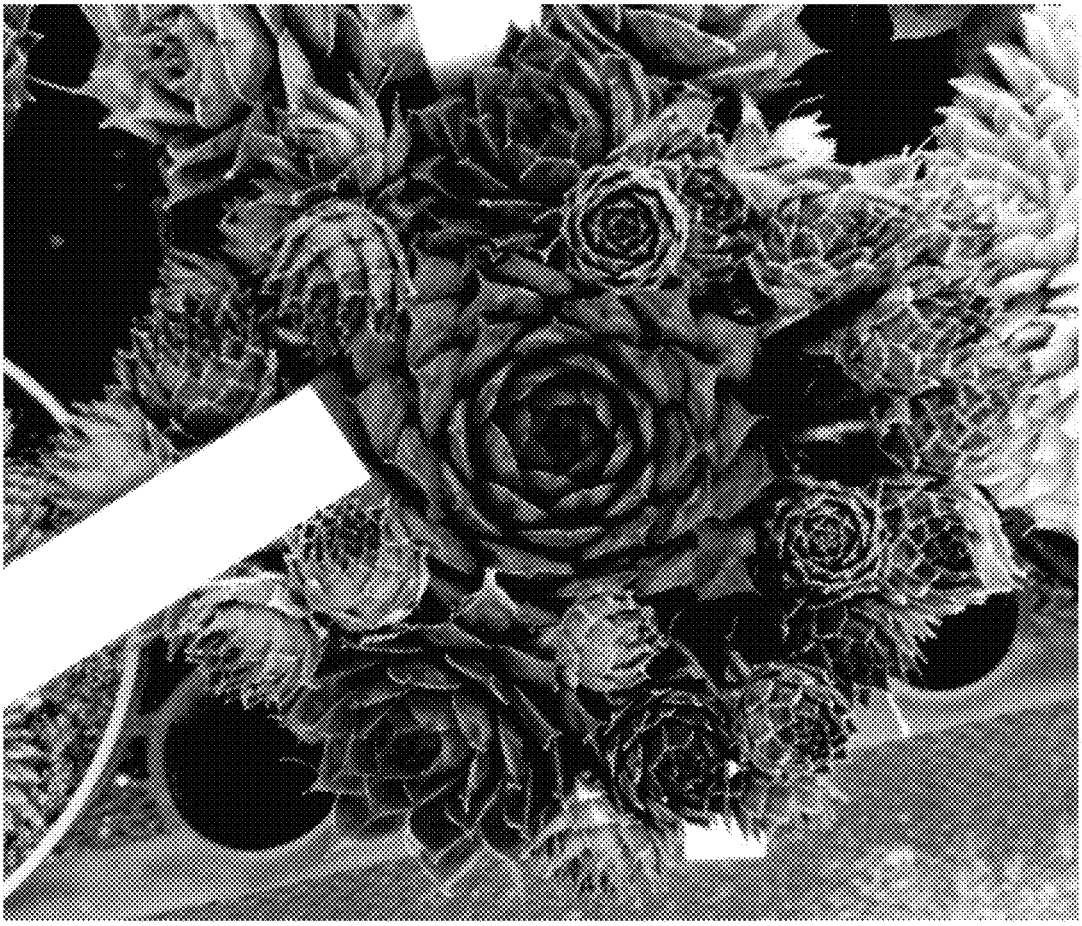

The photograph in FIG. 4 provides a top view of a plant of 'Belsemmag2' in winter.

The colors in the photographs may differ slightly from the color values cited in the detailed botanical description, which accurately describe the colors of the new *Sempervivum.*

DETAILED BOTANICAL DESCRIPTION

The following is a detailed description of the new cultivar as observed on 1.8-year-old plants of the new *Sempervivum* as grown outdoors in 13-cm containers in Westerlo, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen succulent perennial.

*Plant habit*.—Basal rosette, offsets clustered around main rosette.

*Height and spread*.—Reaches up to 7 cm in height and 15 cm in spread and average diameter of main rosette is 7 cm as a 1.8 year-old plant in a container, foliage height can reach up to 10 cm in the landscape.

*Hardiness*.—At least hardy in U.S.D.A. Zones 3 to 9.

*Diseases and pests*.—No susceptibility or resistance to diseases or pests has been observed, *Sempervivums* are generally disease free unless grown under wet and cold conditions.

*Root description*.—Rhizomes grow from main rosette and hold offsets, rounded in shape, average of 2.5 cm in length and 1.5 mm in width, surface texture smooth, glabrous and matte, N199C in color.

*Propagation*.—Cuttings.

*Root development*.—A cutting will root in about 3.5 months and will fully root in a P9 container in about 8 months from a rooted cutting.

*Growth rate*.—Moderate.

Stem description: Stemless.

Foliage description:

*Leaf shape*.—Oblong, succulent.

*Leaf division*.—Simple.

*Leaf arrangement*.—Rosette.

*Leaf quantity*.—70 per rosette.

*Leaf base*.—Broad cuneate.

*Leaf apex*.—Abruptly acute.

*Leaf venation*.—No veins visible.

*Leaf margins*.—Ciliate and un-lobed.

*Leaf attachment*.—Sessile.

*Leaf orientation*.—Slightly curved upward.

*Leaf substance*.—Succulent, average of 2 mm in thickness.

*Leaf surface*.—Both surfaces are smooth and moderately covered with medium length cobweb type pubescence, young foliage is more densely covered with pubescence.

*Leaf color*.—Upper and lower surfaces: spring; young foliage 185A, center of rosette 187A to 187B, tips 185A, mature foliage a blend of 187A, 187B and 187C, tips 185A, summer; young foliage small offsets 145B, tinged with 185B, larger leaves 185B and 145C, mature foliage 187C and 185B, tips and margins 145A to 145B, aging leaves changing to 187C, tips and margins 145B to 145C, autumn; young foliage a blend of 187A and 185B, tips 185A, base 145B, mature foliage 189B, N187A to N187B, tips 185A and 156B, winter; young foliage a blend of 187A to 187B, base 145B, mature foliage N187A, tips 187A to 187B, tips and base 145B, center of rosette 187B, with a hint of 145B.

*Leaf size*.—Average of 3 cm in length and 8 mm in width, 2 mm in thickness.

Flower description: Has not been observed to flower under any tested growing conditions to date.

It is claimed:

1. A new and distinct variety of *Sempervivum* plant named 'Belsemmag2' as described and illustrated herein.

* * * * *